United States Patent
Vogt et al.

(10) Patent No.: US 12,383,703 B2
(45) Date of Patent: Aug. 12, 2025

(54) DEVICE FOR TEMPORARY, LOCAL ADMINISTRATION OF FLUIDS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 779 days.

(21) Appl. No.: 17/025,615

(22) Filed: Sep. 18, 2020

(65) Prior Publication Data
US 2021/0077775 A1    Mar. 18, 2021

(30) Foreign Application Priority Data
Sep. 18, 2019  (EP) ..................................... 19198038

(51) Int. Cl.
*A61M 25/00*  (2006.01)
*A61M 39/20*  (2006.01)
*A61M 39/24*  (2006.01)

(52) U.S. Cl.
CPC .......... *A61M 25/007* (2013.01); *A61M 39/20* (2013.01); *A61M 39/24* (2013.01); *A61M 2205/32* (2013.01); *A61M 2250/00* (2013.01)

(58) Field of Classification Search
CPC .......... A61M 2005/206; A61M 5/2033; A61M 5/2053; A61M 2205/583;
(Continued)

(56) References Cited

U.S. PATENT DOCUMENTS 3,108,595 A * 10/1963 Overment ............. A61M 25/04
                                                          604/105
3,863,641 A *  2/1975 Popa ....................... A61M 1/85
                                                          604/915
(Continued)

FOREIGN PATENT DOCUMENTS

DE      28 43 963       4/1980
DE      32 03 957       8/1983
(Continued)

OTHER PUBLICATIONS

PJ Technologies Medical Devices. "Practical Guide—BeeLine Infusion". <http://beelineinfusion.com/pdf-guide/> (Year: 2023).*
(Continued)

*Primary Examiner* — Scott J Medway
(74) *Attorney, Agent, or Firm* — Dicke, Billig & Czaja, PLLC

(57) ABSTRACT

One aspect relates to a device for local administration of a medical fluid having a hose which is flexibly deformable and has a hose wall. The hose wall has an outer wall of a first material, which is arranged radially to the outside, and the an inner wall of a second material, which is arranged radially to the inside and which delimits an inner conduit of the hose. In a distal portion of the hose, the hose has multiple orifices in the hose wall. The multiple orifices connect the inner conduit with the surroundings of the hose. The distal portion is delimited by a distal end, the device further having a closing element with which the hose is closable. The closing element is manually insertable into the distal end of the hose. A proximal end of the hose is connectable with a container for the medical fluid such that the medical fluid is able to be forced out of the container through the proximal end of the hose into the inner conduit of the hose and forced through the multiple orifices to the surroundings of the hose.

24 Claims, 12 Drawing Sheets

(58) Field of Classification Search
CPC .... A61M 2005/2073; A61M 2205/581; A61M 2005/2013; A61M 5/3202; A61M 5/2046; A61M 2005/31508; A61M 25/007; A61M 2025/0004; A61M 2025/0057

See application file for complete search history.

(56) References Cited

U.S. PATENT DOCUMENTS

| | | | |
|---|---|---|---|
| 3,888,249 A | 6/1975 | Spencer | |
| 3,938,530 A * | 2/1976 | Santomieri | A61M 25/04 604/105 |
| 4,182,326 A * | 1/1980 | Ogle | A61M 3/00 604/203 |
| 4,306,563 A | 12/1981 | Watschenko | |
| 4,347,234 A | 8/1982 | Wahlig et al. | |
| 4,809,710 A * | 3/1989 | Williamson | A61M 25/007 600/593 |
| 4,968,306 A | 11/1990 | Huss et al. | |
| 5,380,307 A | 1/1995 | Chee et al. | |
| 5,425,723 A | 6/1995 | Wang | |
| 5,618,266 A * | 4/1997 | Liprie | A61M 25/1002 604/21 |
| 5,645,528 A | 7/1997 | Thome | |
| 5,792,118 A * | 8/1998 | Kurth | A61M 25/0017 604/246 |
| 5,800,407 A | 9/1998 | Eldor | |
| 5,807,349 A | 9/1998 | Person et al. | |
| 6,024,764 A * | 2/2000 | Schroeppel | A61F 2/04 264/296 |
| 6,045,531 A * | 4/2000 | Davis | A61M 25/0075 604/101.05 |
| 6,132,364 A * | 10/2000 | Rottenberg | A61M 60/569 600/16 |
| 6,245,045 B1 * | 6/2001 | Stratienko | A61M 25/0097 604/164.13 |
| 6,350,253 B1 * | 2/2002 | Deniega | A61M 25/007 604/93.01 |
| 6,537,194 B1 | 3/2003 | Winkler | |
| 8,038,644 B2 * | 10/2011 | Glickman | A61M 25/0017 604/99.01 |
| 8,932,270 B2 * | 1/2015 | O'Day | A61M 25/00 604/523 |
| 9,108,019 B2 * | 8/2015 | Bonnette | A61B 17/32037 |
| 9,138,567 B2 * | 9/2015 | Pruitt | A61M 1/3653 |
| 10,092,693 B2 | 10/2018 | Hanson et al. | |
| 10,188,827 B2 * | 1/2019 | Glickman | A61M 25/007 |
| 10,406,288 B2 | 9/2019 | Reber et al. | |
| 10,555,756 B2 * | 2/2020 | Krieger | A61B 17/3462 |
| 11,511,073 B2 * | 11/2022 | Vogt | A61M 25/0029 |
| 2002/0147480 A1 * | 10/2002 | Mamayek | A61B 18/08 607/105 |
| 2004/0186444 A1 | 9/2004 | Daly et al. | |
| 2004/0210295 A1 * | 10/2004 | Brushey | A61M 25/001 607/120 |
| 2005/0038413 A1 * | 2/2005 | Sansoucy | A61M 25/0075 604/537 |
| 2005/0209563 A1 * | 9/2005 | Hopping | A61M 1/1607 604/151 |
| 2005/0216074 A1 * | 9/2005 | Sahatjian | A61F 2/88 623/1.22 |
| 2006/0155250 A1 | 7/2006 | Endo et al. | |
| 2006/0229573 A1 | 10/2006 | Lamborne | |
| 2007/0149946 A1 * | 6/2007 | Viswanathan | A61M 25/0113 600/585 |
| 2007/0213671 A1 * | 9/2007 | Hiatt | A61M 25/0075 604/164.01 |
| 2007/0232981 A1 * | 10/2007 | Ravenscroft | A61M 25/0075 604/6.16 |
| 2008/0021408 A1 * | 1/2008 | Jacobsen | A61M 25/09016 604/164.13 |
| 2008/0228258 A1 * | 9/2008 | Gerdts | A61F 2/95 604/533 |
| 2008/0300530 A1 | 12/2008 | Massengale | |
| 2009/0254062 A1 * | 10/2009 | McGlothlin | B26F 1/0015 83/13 |
| 2011/0098653 A1 | 4/2011 | Powers et al. | |
| 2012/0179144 A1 * | 7/2012 | Carleo | A61M 25/0017 604/544 |
| 2012/0184921 A1 * | 7/2012 | Brillant | A61M 16/0484 604/533 |
| 2013/0085381 A1 * | 4/2013 | Comerota | A61M 19/00 604/512 |
| 2013/0167839 A1 * | 7/2013 | Vomastek | A61M 16/0463 128/200.26 |
| 2013/0274711 A1 | 10/2013 | O'Day | |
| 2014/0025039 A1 | 1/2014 | Rajendran et al. | |
| 2014/0031741 A1 * | 1/2014 | Stice | A61B 10/0045 604/27 |
| 2014/0081134 A1 * | 3/2014 | Fortson | A61M 25/003 600/435 |
| 2014/0094773 A1 | 4/2014 | Lampropoulos et al. | |
| 2015/0088051 A1 | 3/2015 | Ragg | |
| 2015/0165136 A1 * | 6/2015 | Galgon | B05B 1/1672 128/200.14 |
| 2015/0374929 A1 * | 12/2015 | Hyde | A61M 5/3286 604/239 |
| 2016/0331926 A1 * | 11/2016 | Bueche | B29C 63/42 |
| 2017/0246403 A1 | 8/2017 | Cowe et al. | |
| 2018/0369538 A1 | 12/2018 | Lee et al. | |

FOREIGN PATENT DOCUMENTS

| | | |
|---|---|---|
| DE | 33 34 595 | 4/1985 |
| DE | 34 29 038 | 2/1986 |
| EP | 1932560 | 6/2008 |
| EP | 2 656 869 | 10/2013 |
| JP | H11-506640 | 6/1999 |
| JP | 2004081883 | 3/2004 |
| JP | 2008535578 | 9/2008 |
| JP | 2014500090 | 1/2014 |
| JP | 2014087397 | 5/2014 |
| JP | 2015530153 | 10/2015 |
| JP | 2017529941 | 10/2017 |

OTHER PUBLICATIONS

Adtech. "Expanded PTFE vs PTFE: What's the difference?". <https://adtech.co.uk/about/news/expanded-ptfe-vs-ptfe> (Year: 2023).*

Kühn et al. (K.-D. Kühn, N. Renz, A. Trampuz: Lokale Antibiotika-Therapie (Local antibiotic therapy). Der Unfallchirurg. 120 (2017) 561-572.

K. Klemm: Gentamicin-PMMA-beads in treating bone and soft tissue infections. Zentralbl. Chir. 104(14) (1979) 934-942.

K. Klemm: Antibiotic bead chains. Clin. Orthop. 295 (1993) 63-76.

* cited by examiner

DEVICE FOR TEMPORARY, LOCAL ADMINISTRATION OF FLUIDS

CROSS-REFERENCE TO RELATED APPLICATION

This Utility patent application claims priority to European Application No. 19198038.2, filed Sep. 18, 2019, which is incorporated herein by reference.

TECHNICAL FIELD

One aspect relates to a device for temporary, local administration of medical fluids, in particular of pharmaceutical fluids. One aspect also relates to a method for operating such a device.

BACKGROUND

The local administration of active pharmaceutical ingredients such as antibiotics has already been known for decades and has proven particularly useful in the treatment or easing of bone tissue infections. In this respect, a distinction may be drawn between non-absorbable and absorbable or biodegradable active ingredient vehicles. The introduction of fluids into cavities for the purpose of irrigation and disinfection may however also be useful in the disinfection and cleaning of medical implants and equipment with cavities, the cavities of which would otherwise be difficult to reach.

Absorbable and non-absorbable active ingredient vehicles are known for the medical treatment of infections in hard-to-reach cavities and hollow spaces, such as bone cavities.

The chains of beads known since 1977 by the trade mark Septopal® are an example of non-absorbable active ingredient vehicles. These consist of polymethyl methacrylate beads, which contain the broad spectrum antibiotic gentamicin sulfate, wherein these beads are arranged in chains on steel thread (K. Klemm: Gentamicin-PMMA-beads in treating bone and soft tissue infections. Zentralbl. Chir. 104(14) (1979) 934-942; K. Klemm: Antibiotic bead chains. Clin. Orthop. 295 (1993) 63-76). This chain-type active ingredient vehicle (Septopal®) has for decades proven useful in local antibiotic treatment of osteomyelitis. One advantage is that the gentamicin sulfate is released from the active ingredient vehicle in relatively large quantities over a period of several days. A further advantage is that the chain-type active ingredient vehicle can be straightforwardly adapted by the medical user to the anatomical situation at the implantation site by simply cutting off the steel thread with superfluous beads. One disadvantage is that the active ingredient vehicle exclusively contains gentamicin sulfate and that the medical user cannot modify the active ingredient vehicle with further antibiotics, in accordance with the sensitivity of the microbial microorganisms. In addition, once the bead chain has been implanted delivery of the active pharmaceutical ingredient can no longer be adapted to the course of the treatment without replacing the bead chain. For this reason, successful local treatment in particular of infections with problematic microorganisms, such as MRSA and VRSA, is impossible or only possible to a limited degree. Removal of the bead chains once active ingredient release is complete is associated with considerable stress for the patient due to intergrowth with connective tissue.

Examples of absorbable or biodegradable active ingredient vehicles are nonwovens and sponges of collagen or gelatin. Documents DE 34 29 038 A1, DE 33 34 595 A1, DE 28 43 963 C2, DE 32 03 957 C2 and DE 33 34 595 A1 are stated by way of example. These contain gentamicin sulfate or mixtures of gentamicin sulfate and a gentamicin salt which is sparingly soluble in water. There is moreover a plurality of absorbable or biodegradable active ingredient vehicles based on tricalcium phosphate, hydroxyapatite, gypsum and mixtures thereof and also composite materials of these salts and organic binders. An overview was published by Kühn et al. (K.-D. Kühn, N. Renz, A. Trampuz: Lokale Antibiotika-Therapie (Local antibiotic therapy). Der Unfallchirurg. 120 (2017) 561-572).

One disadvantage of the listed non-absorbable and indeed absorbable or biodegradable active ingredient vehicles is that the antimicrobial active ingredient is fixed by the selected composition and that after implantation of the active ingredient vehicle the active ingredient can no longer be replaced or supplemented by other active ingredients. Furthermore, in all previous local active ingredient release systems, active ingredient release is based on the principle of diffusion, such that large quantities of active ingredient are only released in the first few hours or at most first few days. One exception is the use of sparingly water-soluble active ingredient salts, with which active ingredient release is dependent on the solubility equilibrium of the active ingredient salts.

An active ingredient vehicle is therefore desirable which allows local administration of any desired active pharmaceutical ingredient and wherein the active pharmaceutical ingredient may be replaced at any time by other fluid active pharmaceutical ingredients. Moreover, it is desirable for the active ingredient concentration which is obtained directly at the implantation site to be adjustable directly from outside.

US 2018/0369538 A1 discloses a multilayer catheter for closing blood vessels. Through expansion of an inner layer on contact with liquid, the catheter grows and thus creates a closure. Administration of a liquid is not possible with this catheter. US 2006/0155250 A1 discloses a closure for closing an open end of a catheter for administering a liquid. The closure can be used to close an orifice for feeding a liquid into the catheter when the catheter is not in use. EP 1 932 560 B1 discloses a catheter for administering a medical liquid. The catheter has a hose which has at its distal hose end a plurality of orifices through which a liquid can be administered from inside the hose. Further similar catheters are known from U.S. Pat. No. 5,800,407 A1, U.S. Pat. No. 6,537,194 A1, US 2014/0025039 A1 and U.S. Pat. No. 5,425,723 A1. These catheters have the disadvantage of having a fixed length over which they are able to discharge the medical liquid and they can therefore only be used for specific applications and for treatment situations with specific geometric dimensions. The catheters thus have only very slight variability for adaptation to the treatment situation. In addition, delivery of the medical liquid is only adjustable by using a slowly diminishing pressure, wherein the pressure is dependent on the elasticity of the liquid-containing walls of the catheter. Rapid, short-term delivery of the medical liquid is not possible. Furthermore, with extended use of the catheter (for longer than one day) the tissue surrounding the catheter may grow into the orifices and so cause considerable problems on withdrawal/removal of the catheter. The surrounding tissue may thus be damaged by removal of the catheter, so reducing treatment success.

For these and other reasons there is a need for the present embodiment.

SUMMARY

The subject of one embodiment is in particular a medical device for temporary, local administration of pharmaceutical fluids or other medical fluids over a period of hours up to several days. Depending on the respective geometric requirement and/or the anatomical situation of the implantation site, the device according to one embodiment may be adapted with regard to length by simple mechanical shortening without a loss in function. Furthermore, a device is proposed for continuous discharge of medical fluids which can advantageously be combined with the device for local administration of medical fluids such that pharmaceutical fluids or other medical fluids can be continuously administered locally over a period of hours to days.

BRIEF DESCRIPTION OF THE DRAWINGS

Further exemplary embodiments of the embodiments are explained below with reference to twelve schematically depicted figures, but without thereby restricting the invention. In the figures.

DETAILED DESCRIPTION

Figure 1:
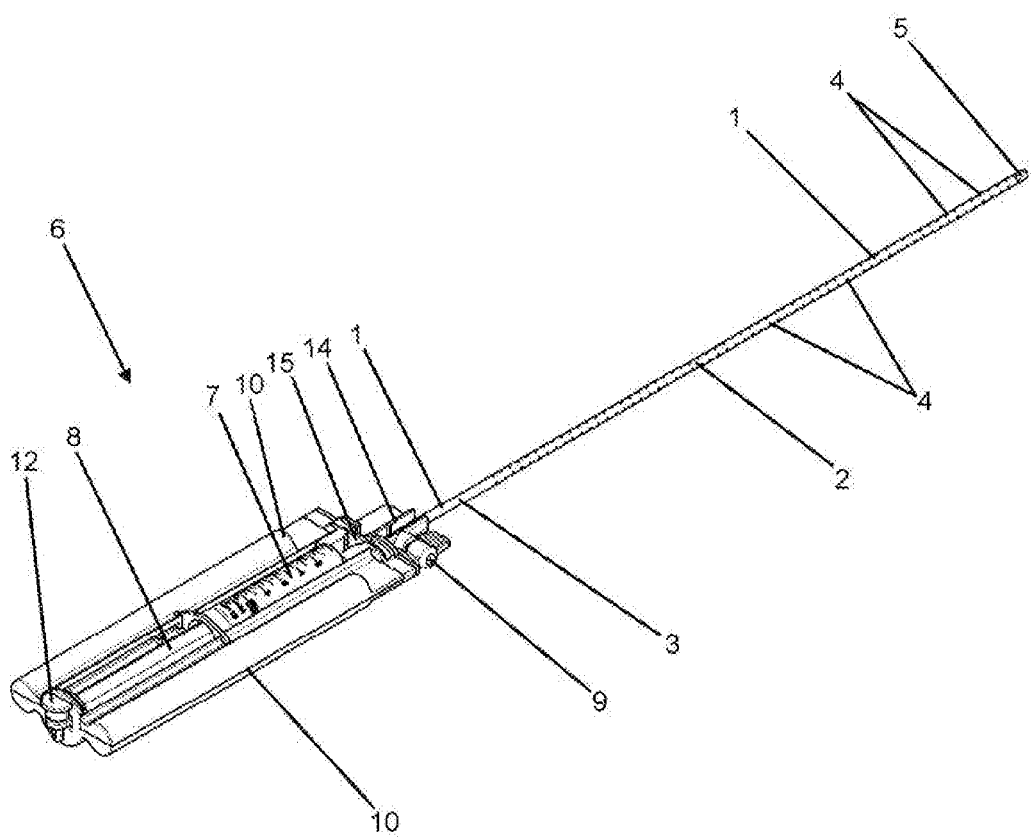
FIG. 1 is a schematic perspective view of a first exemplary device according to the embodiment for local administration of a fluid.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

The object of one embodiment is to overcome the disadvantages of the prior art. The intention in one embodiment is in particular to provide a device for local administration of medical fluids, in particular of pharmaceutical fluids, such as for example antibiotic solutions, which enables local and temporary delivery of the medical fluid in regions which are difficult to access, such as for example cavities of non-implanted implants or other medical devices. The device in one embodiment is intended to be flexibly adaptable to different fields of application. Mechanical loading of the walls of the cavities to be irrigated is to be avoided as far as possible. In the case of use to treat an infection, the intention is to ensure maximally gentle treatment, in which the adjacent inflamed tissue is irritated as little as possible, both during temporary delivery of the fluid and during insertion and removal of the introduced part of the device. The device is also intended to be suitable for repeated delivery of the fluid over relatively long periods at a specific site without the device having to be removed for this purpose. The device is intended to be inexpensive to manufacture and as far as possible to be a hygienic, single-use, disposable product. At least the part of the device placeable into the cavity to be irrigated or indeed the entire device is intended to be inexpensively and readily disposable of as a disposable product.

The object of one embodiment thus also consists in developing a simple, inexpensive device for local administration of medical fluids. The device is intended to enable local administration in particular of pharmaceutical fluids of any desired composition, for example antibiotic solutions. In the case of medical application after implantation, one part of the device is in the patient and a second part of the device is outside the patient. The medical fluids are intended to be introducible in the part of the device located outside the patient and then conveyed by the device to the implantation site and released there. The device is intended to be plastically deformable, in order to be able to follow the anatomical conditions at the implantation site or the geometric shape of the hollow shape. Once shaping by the medical user is complete, the shape of the device cannot be modified apart from by manual deformation by the medical user.

The release of pharmaceutical fluids is intended to proceed from orifices arranged along the device. The orifices are intended to be reversibly closable in order to prevent backflow of contaminated fluid into the interior of the device or to prevent ingrowth of connective tissue or clogging of the orifices by coagulated blood. The device is moreover intended to be constituted such that the part of the device optionally located in the patient may be adapted to the patient's respective anatomical situation by shortening the length, without the function of the device being impaired.

The device should moreover not change significantly with regard to shape and also with regard to diameter on administration of the medical fluid or of the pharmaceutical fluid. Significant transverse expansion could otherwise cause the patient pain in the inflamed or infected tissue. Furthermore, the intention is to develop a simple inexpensive device which enables continuous discharge of medical fluids, in particular of pharmaceutical fluids, over a period of hours to days, without electric motors, batteries or storage batteries being needed.

The object of one embodiment is achieved by a device for local administration of a medical fluid, having a hose, which is flexibly deformable and which has a hose wall, wherein the hose wall has an outer wall of a first material which is arranged radially to the outside, and the hose wall has an inner wall of a second material which is arranged radially to the inside and which delimits an inner conduit of the hose, wherein, in a distal portion of the hose, the hose has multiple orifices in the hose wall, wherein the multiple orifices connect the inner conduit of the hose with the surroundings of the hose, wherein the distal portion of the hose is delimited by a distal end of the hose, wherein, in a proximal portion of the hose, the hose does not have any orifices in the hose wall which connect the inner conduit of the hose with the surroundings of the hose in a liquid-permeable manner, the device further having a closing element with which the hose is closed or closable in liquid-tight manner at the distal end of the hose, wherein the closing element is manually insertable into the distal end of the hose, wherein a proximal end of the hose is connected or connectable to a container for the medical fluid, in a liquid-permeable manner, in such a way that the medical fluid is pressable out of the container through the proximal end of the hose into the inner conduit of the hose and pressed out to the surroundings of the hose through the multiple orifices.

Medical instruments and non-implanted implants may also be washed off or washed out using the device, in particular medical instruments and implants with cavities into which the hose may be introduced. The device may however also be used for free distribution of the medical fluid. Particularly suitable, however is a medical application of the device according to one embodiment in which the hose is introduced into a cavity of a human body and the fluid is used to treat the adjoining tissue.

The device according to one embodiment is preferably a medical device.

In one embodiment, the first material and the second material preferably differ from one another with regard to at least one material property. Particularly preferably, the first material and the second material differ from one another with regard to elasticity and/or hardness.

According to one embodiment, the second material may be a rubber-elastic material, while the first material is more dimensionally stable than the second material. For example, the inner wall may be a coating with a rubber-elastic material on the inside of the outer wall.

The statements of direction "distal" and "proximal" relate in the present case to the intended direction of flow of the medical fluid when in use. The medical fluid flows in this case from a proximal end of the hose towards the distal end of the hose and there out of the multiple orifices.

The hose wall may take the form of a jacket.

The outer wall may surround the inner wall in the manner of a jacket.

The hose is in one embodiment cylindrical in shape apart from the multiple orifices. The hose wall then delimits the hose in one embodiment at its cylindrical circumferential surface. With straight hoses with a cylindrical geometry the circumferential surface is the wall perpendicular to the cylinder axis of the cylindrical hose. The orifices are thus located in the circumferential surface.

Provision may further be made for the proximal portion of the hose to be delimited by the proximal end of the hose.

Provision may moreover be made for the hose to be gas-tightly and/or pressure-tightly closed or closable with the closing element at the distal end.

In one embodiment, a pharmaceutical fluid is preferably used as the medical fluid. A pharmaceutical fluid contains at least one active pharmaceutical ingredient. Solutions containing at least one antibiotic, at least one cytostatic, at least one chemotherapeutic agent and/or at least one antimycotic are particularly preferred as pharmaceutical fluids or medical fluids. Alternative medical fluids may contain disinfecting constituents. The term "pharmaceutical fluid" should accordingly be understood to mean aqueous and also non-aqueous solutions and suspensions of active pharmaceutical ingredients. Furthermore, the term "pharmaceutical fluid" also covers mixtures and solutions of gases in water, liquids containing water and non-aqueous liquids. The term "pharmaceutical fluid" in one embodiment also includes gases and gas mixtures.

Provision may also be made for at least one of the multiple orifices to be arranged in the region of the distal end of the hose, in one embodiment to be arranged within 5 mm of the distal end of the hose, in one embodiment to be arranged within 3 mm of the distal end of the hose.

The multiple orifices arranged in the hose wall are in one embodiment at least three orifices.

Provision may in one embodiment be made for an X-ray opaque material to be contained in the closing element or for the closing element to consist of an X-ray opaque material. The X-ray opaque material may in one embodiment be selected from stainless steel, special steel, titanium, titanium alloys, tantalum, tantalum alloys, barium sulfate, plastics containing barium sulfate, zirconium dioxide and plastics containing zirconium dioxide.

In devices according to one embodiment provision may be made for the inner conduit of the hose to begin at a proximal opening in the proximal end of the hose and to end at a distal opening in the distal end of the hose, wherein the distal opening of the hose is closed or closable by the closing element.

The inner conduit may in this way connect the two open ends, namely the distal end and the proximal end of the hose. In this way, the medical fluid may be passed through the inner conduit of the hose and administered through the multiple orifices in the hose wall.

Provision may moreover be made for the device to include the container for the medical fluid, wherein the container in one embodiment includes a hollow cylinder with a plunger displaceable axially in the hollow cylinder, the plunger closing a first end of the hollow cylinder, wherein the hollow cylinder has a discharge opening at an opposite end from the first end, the discharge opening being connected or connectable with the proximal end of the hose, in one embodiment being connected or connectable with the proximal end of the hose via a manually operable valve element for regulating the flow velocity of the medical fluid.

This means that no separate reservoir for the medical liquid has to be connected to the device. The plunger is in one embodiment drivable with at least one tensioned elastic spring.

In this respect, provision may be made for a medical fluid, in particular a pharmaceutical fluid, to be contained in the container.

In this way, the device is directly usable for producing a flow of medical fluid out of the multiple orifices.

Provision may in one embodiment moreover be made for the device to have a delivery means, with which the medical fluid is able to be forced out of the connected or connectable container into the hose, through the inner conduit of the hose and through the multiple orifices into the surroundings of the hose.

The device may thus also be used to drive the flow of medical liquid. With such a device it is possible to administer pharmaceutical fluids locally over a period of hours up to several days without the need for complex electrically operated pump systems. The medical fluid may in one embodiment be delivered discontinuously or continuously with the delivery means.

In devices with delivery means, provision may in one embodiment be made for the delivery means to have an energy storage element, in particular, at least one tensioned spring, wherein the delivery means is drivable with energy from the energy storage element, wherein in one embodiment, a plunger is drivable with the energy storage element in a hollow cylinder towards an opposing discharge opening.

This means that the device does not have to be connected to an external power supply to drive the delivery means. A tensioned spring contains sufficient energy to enable the device to expel a quantity of a few milliliters to a few centiliters of the medical fluid.

Provision may also be made for the outer wall and the inner wall to be fixedly connected to each other, in one embodiment connected to each other over the entire surface.

In this way, the outer wall and the inner wall are immobilized relative to one another. This makes it possible for the multiple orifices in the inner wall to be closable owing to elastic stress relief without medical fluid pressure in the inner conduit, while the outer wall may absorb the pressure which is needed to open the multiple orifices in the inner wall.

For active fluid delivery, provision may be made for the sum of the free cross-sectional areas of all the multiple orifices to be at most as large as the free cross-section of the inner conduit.

In this way, it is ensured that medical fluid may also flow through the orifices of the multiple orifices arranged at the distal end of the hose. It is thus ensured that medical fluid also exits from the orifices arranged at the distal end. The sum of the free cross-sectional areas of all the multiple orifices relates to the open state of the multiple orifices.

Provision may moreover be made for the multiple orifices in the outer wall of the hose wall to be open irrespective of the pressure applied by the medical fluid, while the multiple orifices in the inner wall of the hose wall are closed when no pressure is applied by the medical fluid and are openable in a fluid-permeable manner by applying pressure on the medical fluid. In this way, the multiple orifices in the hose wall close if no medical liquid is forced into the inner conduit. In the case of intermittent operation, it is thus possible to prevent tissue from growing through the multiple orifices into the inner conduit, so causing the device to grow together with the cavity.

Provision may in one embodiment also be made for the outer wall of the hose wall to absorb a pressure from the medical fluid in the inner conduit imparted via the inner wall of the hose wall, without expanding radially by more than 5%, in one embodiment without expanding radially by more than 1%.

The pressure from the medical fluid may not rise above 500 kPa under normal conditions for normal applications of the device according to one embodiment. Provision may thus be made for the outer wall of the hose wall to absorb in the inner conduit a hydrostatic pressure of at most 500 kPa imparted via the inner wall of the hose wall, without expanding radially by more than 5%, in one embodiment without expanding radially by more than 1%.

In this way, it is ensured that the hose does not expand too much when the medical fluid is forced through the hose. This prevents irritation of the surrounding tissue or mechanical loading of the surrounding structures.

It is also proposed within one embodiment that the hose expand radially by at most 5 percent under an internal pressure of 500 kPa relative to normal pressure, in one embodiment by at most 1 percent under an internal pressure of 500 kPa relative to normal pressure.

In this way, it is ensured that the hose does not expand too much when the medical fluid is forced through the hose. This prevents irritation of the surrounding tissue or mechanical loading of the surrounding structures.

Provision may moreover be made for the closing element to have a conical or cylindrical projection which is inserted or screwed into the hose, such that the hose is clamped in the region of the distal end of the outer hose by the projection in such a way that the hose is closed in fluid-tight manner at the distal end of the hose, wherein the conical or cylindrical projection in one embodiment has ribs on the outside of the projection or the conical or cylindrical projection has an external thread, wherein the external thread or the conical or cylindrical projection has a larger external diameter then the internal diameter of the hose.

In this way, the distal end of the hose may be reliably sealed even after the distal portion of the hose has been shortened.

According to one embodiment, provision may be made for the multiple orifices in the distal portion of the hose in the outer wall to have a diameter of at most 500 µm, in one embodiment of at most 250 µm and in one embodiment of at most 100 µm.

The diameter here relates to the average diameter of the opening cross-section of the multiple orifices. If the inner wall is configured to close the multiple orifices when in the unstressed state, i.e. without the application of pressure, the diameter of the inner wall is naturally smaller at least in the closed state. When the multiple orifices in the inner wall are open, the diameter of the multiple orifices in the inner wall is at most as great as the diameter of the multiple orifices in the outer wall.

With orifices with such maximum diameters, it is ensured that the through-flow rates of the medical fluid are not too high and on the other hand the free line cross-section of the inner conduit is sufficient to be able to use even the orifices close to the distal end of the hose only for delivery of the medical fluid.

One embodiment, may also be distinguished in that the hose is formed of a coaxial coextrudate, wherein the inner wall consists of a rubber-elastic polymer, in particular polyurethane or a weakly crosslinked polymer, and the outer wall consists of a non-rubber-elastic thermoplastic polymer or of a highly crosslinked polymer, in particular of polyamide.

This ensures that the orifices are closed by the inner wall if no hydrostatic pressure is exerted on the inner wall, and the orifices in the inner wall open when the pressure exerted by the medical fluid increases. In this way, ingrowth of tissue and contamination of the inner conduit via the orifices may be prevented.

In one embodiment, coextruded hoses are particularly preferred in which the inner wall consists of a rubber-elastic polyurethane and the outer wall is formed from thermoplastic, non-rubber-elastic polyamide. The multiple orifices pass through the inner wall and the outer wall. When pressure is applied by a medical fluid the orifices in the inner wall are released by elastic yielding of the elastic polyurethane and the medical fluid may exit from the outer wall through the orifices in the rigid polyamide. On completion of fluid discharge, the orifices in the inner wall of the hose close again and body fluids, such as for example blood or wound exudate, cannot penetrate into the inner conduit of the hose. During fluid discharge, the rigid, non-elastic outer wall prevents radial expansion of the hose. In this way, no forces are exerted on the tissue to be treated and pain as a result of a mechanical action is prevented, or no forces are transmitted to the walls of the irrigated implant or cavity.

Provision may also be made for an X-ray opaque material to be present in the hose at least at the distal end of the hose and/or in the closing element, in one embodiment an X-ray opaque material is present in the distal portion of the hose and/or in the closing element, in one embodiment is present over the entire length of the distal portion of the hose and in the closing element or is present over the entire length of the hose and in the closing element.

In this way, the position and situation of the hose can be visualized by X-ray methods and the hose positioned under X-ray control and the position of the device in the patient thereby unambiguously determined by radiography.

The X-ray opaque material may in one embodiment be selected from special steel, titanium, titanium alloys, tantalum, tantalum alloys, barium sulfate, plastics containing barium sulfate, zirconium dioxide and plastics containing zirconium dioxide.

Provision may moreover be made for at least one metal wire, at least one metal coil and/or at least one metal mesh to be arranged in the inner conduit of the hose and/or in the hose wall of the hose, wherein the at least one metal wire, the at least one metal coil and/or the at least one metal mesh are in one embodiment arranged along the entire length of the hose.

The at least one metal wire, the at least one metal coil and the at least one metal mesh serve in the plastic deformability of the hose. In this way, the shape of the hose may be modified and thus adapted to the respective situation, without the surroundings of the device being mechanically stressed, wherein the shape of the hose is retained by the at least one metal wire, the at least one metal coil and/or the at least one metal mesh. In this way, the device keeps its shape after previous shaping in accordance with anatomical conditions. This enables site-specific administration of pharmaceutical fluids to precisely predetermined implantation sites. In addition, the metallic structures are discernible in the X-ray image.

Provision may in one embodiment also be made for the closing element to have the following features: a rotationally symmetrical first body with external thread or with circumferentially extending ribs, wherein the external thread or the ribs has/have a larger external diameter than the internal diameter of the hose, a rotationally symmetrical second body with an external diameter less than or equal to the external diameter of the hose, wherein the axial extent of the second body is at least 5 mm, wherein the rotationally symmetrical first body is connected axially with the rotationally symmetrical second body.

In this way, the hose may be reliably closed in liquid-tight manner with the closing element.

Provision may furthermore be made for the closing element to be screwed or pressed into the distal end of the hose and to close the free line cross-section of the inner conduit of the hose at the distal end completely and in liquid- and pressure-tight manner.

In this way, it is ensured that sufficient pressure can be built up in the inner conduit with the medical fluid to be able to force the medical liquid out of all the multiple orifices. The closing element in one embodiment also closes the distal end of the hose in gas-tight manner.

Provision may moreover be made for a valve element, in particular a non-return valve, to be arranged at the proximal end of the hose or in the connection to the container for the medical fluid, the valve preventing flow of the medical fluid towards the container and allows flow of the medical fluid out of the container towards the distal portion.

In this way, it is ensured that no contaminated medical fluid can penetrate from the inner conduit into the container for the medical fluid.

Provision may also be made for all, pairs or groups of the multiple orifices to be spaced relative to one another in the axial direction of the hose.

In this way, the medical fluid may exit at various points spaced axially from one another. In addition, the distal portion of the hose may be shortened in length at various points, wherein at the same time at least one orifice of the multiple orifices is always present in the distal portion of the hose.

Provision may in one embodiment also be made for the hose to be plastically deformable and/or to have an external diameter of less than or equal to 7 mm, in one embodiment an external diameter of between 2 mm and 4 mm.

As a result of the small external diameter, the hose can be readily introduced into cavities in implants and into cavities in the human body and there be suitable for washing out the cavities. The plastic deformability prevents an elastic force from acting on the walls of the cavity to be irrigated and loading it mechanically.

Provision may moreover be made for the first material to have a greater Shore A hardness than the second material, wherein the first material in one embodiment has a Shore A hardness of more than 60 and the second material a Shore A hardness of less than 60.

Shore A hardness is determined to DIN ISO 7619-1 (2012 February) [2]. Using materials with these differences in hardness ensures that the inner wall may close the multiple orifices in the outer wall.

Provision may further be made for the multiple orifices in the inner wall to have a free cross-section greater by a factor of two or more when pressure with a hydrostatic pressure of 500 kPa is applied thereto by the medical fluid compared to without applying pressure.

In this way it is ensured that the multiple orifices in the inner wall are openable by the pressure of the medical fluid.

Provision may be made for the multiple orifices in the inner wall or the outer wall to be slit-shaped.

These two measures ensure that the slit-shaped orifices may be opened by a pressure acting on the medical fluid and close again on reduction of the pressure on the medical fluid. In this way, tissue is prevented from growing into the multiple orifices during intermittent operation. Contamination of the medical fluid in the inner conduit may also be prevented in this way. The multiple orifices in the inner wall are in one embodiment slit-shaped. This has the advantage that deformation thereof does not cause any deformation of the outer faces of the hose.

According to one embodiment, provision may be made for the multiple orifices in the inner wall to be reversibly closable in fluid-tight manner as a function of a physical quantity acting on the second material, in particular as a function of a pressure from the medical fluid acting on the second material, or for the multiple orifices in the outer wall to be reversibly closable in fluid-tight manner as a function of a physical quantity acting on the first material, in particular as a function of a pressure from the medical fluid acting on the first material.

In the second case the pressure in the open parts of the multiple orifices in the inner wall may act on the first material of the outer wall. In one embodiment, the first material and the second material are selected such that the multiple orifices in the inner wall are reversibly closable in fluid-tight manner as a function of a physical quantity acting on the second material, in particular as a function of a pressure from the medical fluid acting on the second material, or for the multiple orifices in the outer wall to be reversibly closable in fluid-tight manner as a function of a physical quantity acting on the first material, in particular as a function of a pressure from the medical fluid acting on the first material.

These measures enable the multiple orifices to be opened and closed reversibly. In addition to the pressure, an electrical voltage or mechanical stress, a magnetic field or a temperature (if shape-memory alloys are used, for example) may for example be used to open and close the multiple orifices.

Provision should furthermore be made for the multiple orifices to be reversibly openable by elastic deformation of the second material, while the multiple orifices in the first material remain open, wherein the first material is in one embodiment dimensionally stable such that the outer wall absorbs at least some of the forces caused by the elastic deformation of the second material and so counteracts radial deformation of the hose.

This ensures that the hose is not or is only very slightly radially deformed.

Alternatively, provision may also be made for the multiple orifices to be reversibly openable by elastic deformation of the first material, while the multiple orifices in the second material remain open, wherein the second material is in one embodiment dimensionally stable such that the inner wall absorbs at least some of the forces caused by the elastic deformation of the first material and so counteracts radial deformation of the hose.

The objects underlying one embodiment are also achieved by a method for operating a medical device for local administration of a medical fluid, the device having a hose with a hose wall, wherein the hose wall has an outer wall of a first material which is arranged radially to the outside, and the hose wall has an inner wall of a second material which is arranged radially to the inside and which delimits an inner conduit of the hose, wherein the hose has multiple orifices in the hose wall, wherein the multiple orifices connect the inner conduit of the hose with the surroundings of the hose, the method having the following steps:
A) introducing a medical fluid into the hose;
B) exerting pressure on the medical fluid in the hose;
C) opening the multiple orifices in the inner wall or in the outer wall of the hose through the pressure of the medical fluid acting on the multiple orifices; and
D) expelling medical fluid through the open multiple orifices.

The steps are in one embodiment performed chronologically one after the other.

After step D) the pressure on the medical fluid may be reduced and the multiple orifices thereby closed.

Provision may be made for the method not to involve any medical treatment of a human or animal body and/or for the medical fluid not to be delivered to a human or animal body in the context of the method.

It is hereby clarified that the method according to one embodiment is not a method for treating the human body.

Step E) reducing the pressure on the medical fluid in the hose after step D) and thereby closing the multiple orifices in the inner wall or in the outer wall of the hose or reducing the free cross-section of the multiple orifices in the inner wall or in the outer wall of the hose may moreover be provided.

In this way, the method may be used intermittently without the medical fluid in the inner conduit being contaminated with back-flowing fluids.

Provision may furthermore be made for the hose to be shortened by cutting off prior to step A) and a closing element to be inserted or screwed into the end of the hose which has just been cut, wherein the closing element seals the hose in fluid-tight manner, in one embodiment closes it in fluid-tight and pressure-tight manner.

In this way, the hose may be brought simply to a length suitable for the application.

Provision may finally be made for the method to be carried out with a device according to one embodiment.

In this way, the method has the advantages mentioned in the respective claims.

One embodiment is based on the surprising recognition that it is possible, with the assistance of a hose with an inner wall and an outer wall of different materials, reversibly to open and close the multiple orifices present in the hose wall as a function of the pressure of a medical fluid or as a function of other physical status variables, effects or fields, in order in this way temporarily to deliver a medical fluid. It is possible to close or open the multiple orifices by acting on just the inner wall or on just the outer wall of the hose. At the same time, no forces are exerted on the outer wall or deformation of the external shape of the hose is avoided. In this way, the hose remains externally dimensionally stable. Mechanical loading of the adjoining surfaces to be treated with the medical fluid is avoided in this way. The valve provided in this way may thus be opened and closed again without changing the external shape of the hose. In this way, mechanical irritation of adjoining inflamed tissue, for example, may be prevented or at least reduced. In particular when the multiple orifices are only opened for fluid passage when opened by the pressure of the medical fluid, the multiple orifices and thus the device are closed without further feed-in of the medical fluid.

A further surprising recognition is that the hose can be shortened without difficulty and in this way the length thereof may be adapted to the respective situation. To this end, the distal end of the hose has merely to be closed with an existing or a new closing element. The device can be inexpensively made completely or largely from plastics and may in this way be provided as a hygienic single-use product. The multiple orifices in the hose are closed in such a way that, in the closed state, no undercuts arise in the interspace between the outer wall and the inner wall into which the tissue could grow and so make it difficult to remove the device or the hose.

The device in one embodiment has a valve function to be actuated outside the patient. Depending on the anatomical situation of the implantation site or the depth of the cavity, the device according to one embodiment may be adapted with regard to its length by simple mechanical shortening, without losing function.

The particular advantage of the device according to one embodiment consists in the fact that the medical user may apply any desired medical fluid in a precisely defined volume. For fluids containing active ingredients, one or more pharmaceutical active ingredient substances may be adjusted in the fluid in precisely predetermined concentrations. This makes it possible to achieve and thus to treat with precisely defined active ingredient concentrations in the immediate vicinity of the orifices of the device. A further advantage of the device is that the multiple orifices in the hose are only opened during administration and closed thereafter, such that no blood or tissue fluid and also no connective tissue which forms can penetrate into the interspace between the inner wall and the outer wall and there form undercuts which tear on removal of the device and thereby cause fresh irritation of the tissue which has just been treated. In addition, blockages of the device, in particular of the orifices in the hose, are avoided.

An exemplary device according to one embodiment for local administration of fluids with valve function is composed of
- a) a plastically deformable hose, wherein the hose is subdivided into a distal portion and a proximal portion,
- b) wherein the distal portion of the hose has at least two orifices in the circumferential surface, which connect the interior of the hose with the surroundings, wherein the sum of the cross-sectional areas of the orifices is equal to or less than the internal cross-section of the hose,
- c) the proximal portion of the hose does not contain any orifices in the circumferential surface which connect the interior of the hose with the surroundings,
- d) a manually insertable closing element, which closes a distal end of the distal portion of the hose in liquid- and gas-tight manner, and
- e) a distal hose end of the proximal portion of the hose, which is connectable or connected in liquid-tight manner with an active ingredient reservoir discontinuously or continuously delivering active ingredient solution.

The closing element is composed for example of a first rotationally symmetrical body with external thread, wherein the external thread has a larger external diameter than the internal diameter of the hose, and of a second rotationally symmetrical body with an external diameter less than or equal to the external diameter of the outer hose, wherein the axial extent of the second rotationally symmetrical body is at least 5 mm, and wherein the first rotationally symmetrical body is connected axially with the second rotationally symmetrical body.

In a further alternative embodiment, an exemplary closing element is composed of a first rotationally symmetrical body with circumferentially extending ribs, wherein the ribs have a larger external diameter than the internal diameter of the inner hose, and of a second rotationally symmetrical body with an external diameter less than or equal to the external diameter of the outer hose, wherein the axial extent of the second rotationally symmetrical body is at least 5 mm, and wherein the first rotationally symmetrical body is connected axially with the second rotationally symmetrical body.

In the figures and the following description of the exemplary embodiments explained with reference to the figures, some of the same reference signs are used for the same or similar parts in different exemplary embodiments so as to simplify comparability of the exemplary embodiments and readability.

Figure 11:
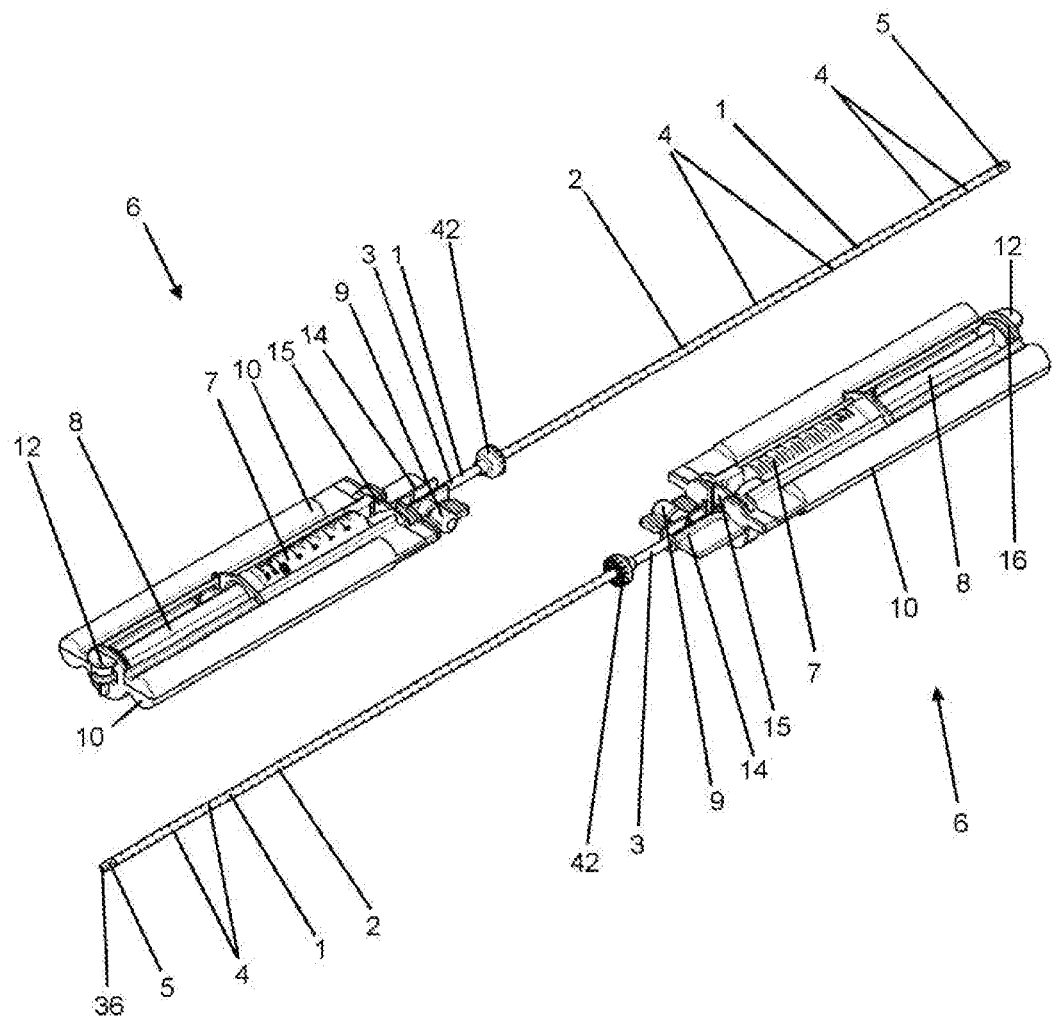
FIG. 11 illustrates two schematic, perspective views of an exemplary further device according to the embodiment for local administration of a fluid.
Figure 12:
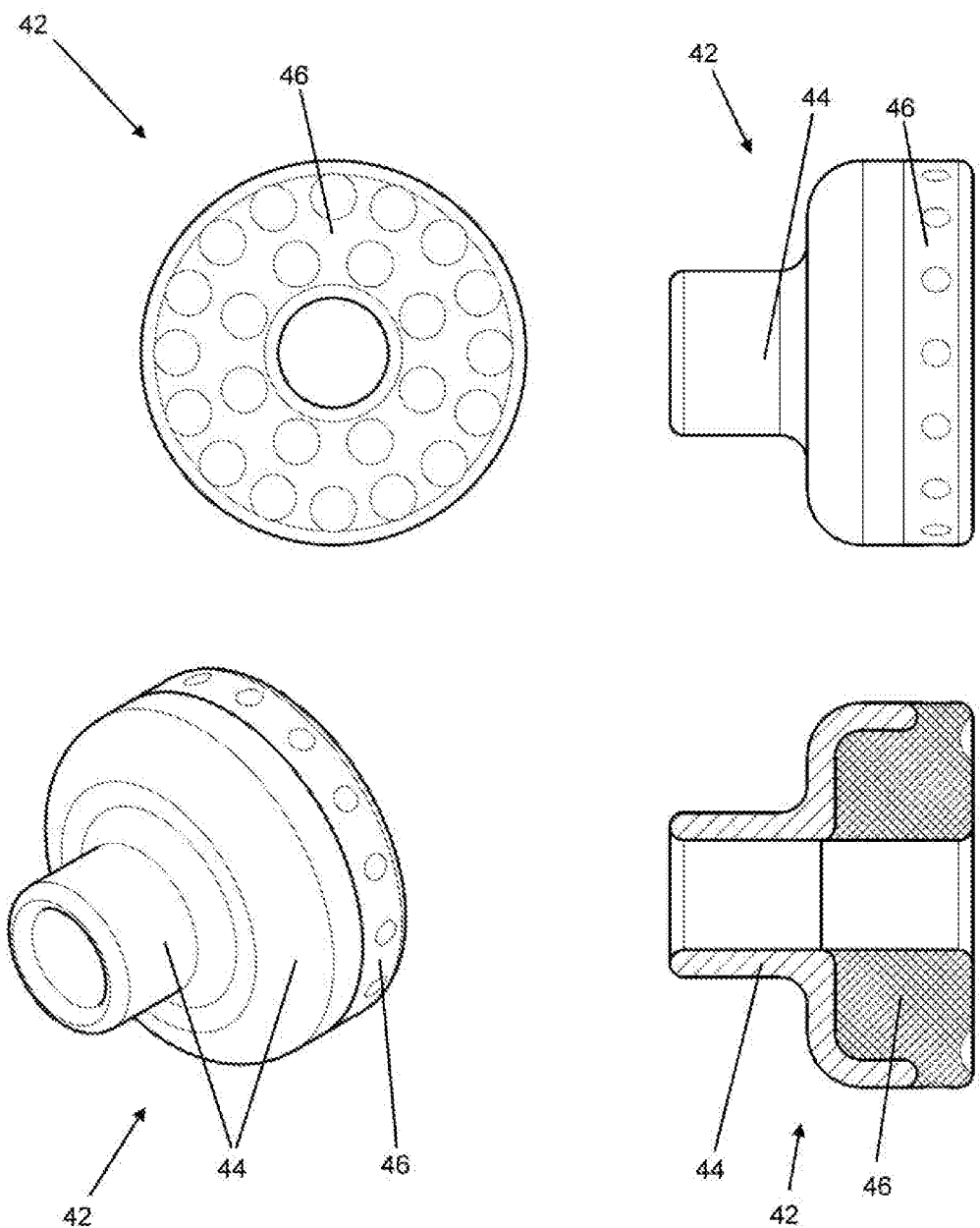
FIG. 12 illustrates four schematic detail views of a limit stop element of the exemplary embodiment according to FIG. 11.

FIGS. 1 to 6 illustrate a first exemplary device according to one embodiment and parts thereof in different representations. FIGS. 7 to 10 illustrate open and closed distal hose end pieces as parts of two different exemplary embodiments according to one embodiment. FIGS. 11 and 12 illustrate a further exemplary embodiment according to one embodiment.

The first exemplary device according to one embodiment, which is illustrated in FIGS. 1 to 6, has at the front distal end (top right in FIG. 1) a hose 1 with a distal portion 2 and a proximal portion 3. In the distal portion 2 of the hose 1 it is possible to arrange a plurality of orifices 4 passing through the hose wall, which orifices extend as far as into an inner conduit 30 (not visible in FIGS. 1 to 6, but visible in FIGS. 7 to 10) of the hose 1. The hose 1 may be plastically deformable, such that the shape of the hose 1 may be adapted to the shape of a cavity to be irrigated. The proximal portion 3 of the hose 1 does not have any orifices in the hose wall. It is thus ensured that a medical fluid (not illustrated) administered with such a device only exits within the cavity to be irrigated.

The distal portion 2 of the hose 1 may be closed at a distal end in fluid-tight and pressure-tight manner with a closing element 5. The hose 1 has an inner wall 40 and an outer wall 38 (not visible in FIGS. 1 to 6 but constructed in a similar manner to in FIGS. 9 and 10), wherein the outer wall 38 encloses the inner wall 40, in one embodiment coaxially. The orifices 4 extend through the outer wall 38 and the inner wall 40. In the interior of the hose 1 the inner conduit 30 is in one embodiment delimited by the inner wall 40. The orifices 4 may connect the inner conduit 30 with the surroundings of the hose 1 in liquid-permeable manner. The inner wall 40 may consist of an elastically deformable material such as a rubber-elastic polymer, in particular polyurethane. The outer wall 38 may consist of a non-rubber-elastic thermoplastic polymer, in particular of polyamide. This makes the inner wall 40 elastically deformable, while the outer wall 38 is largely dimensionally stable with regard to radial expansion of the hose 1. The material for the outer wall 38 may be selected such that deformation of the longitudinal axis of the hose 1 is possible, while radial expansion of the hose 1 through internal pressure in the inner conduit 30 is not possible or only at most five percent relative axial extension is possible.

Figure 2:
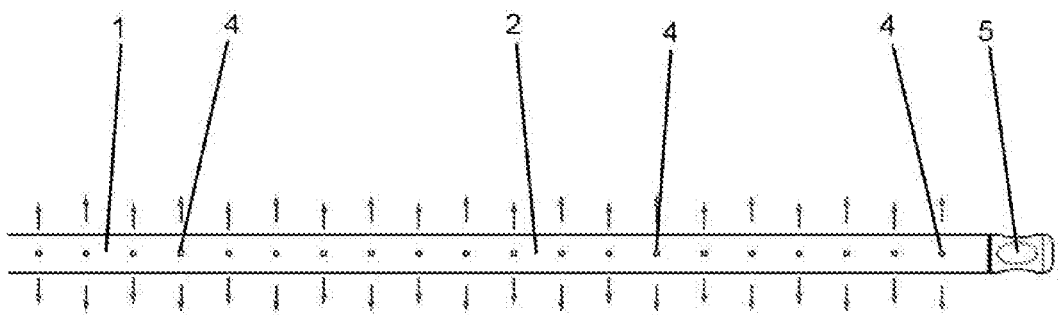
FIG. 2 illustrates a schematic side view of a distal end of the device according to FIG. 1.
Figure 3:
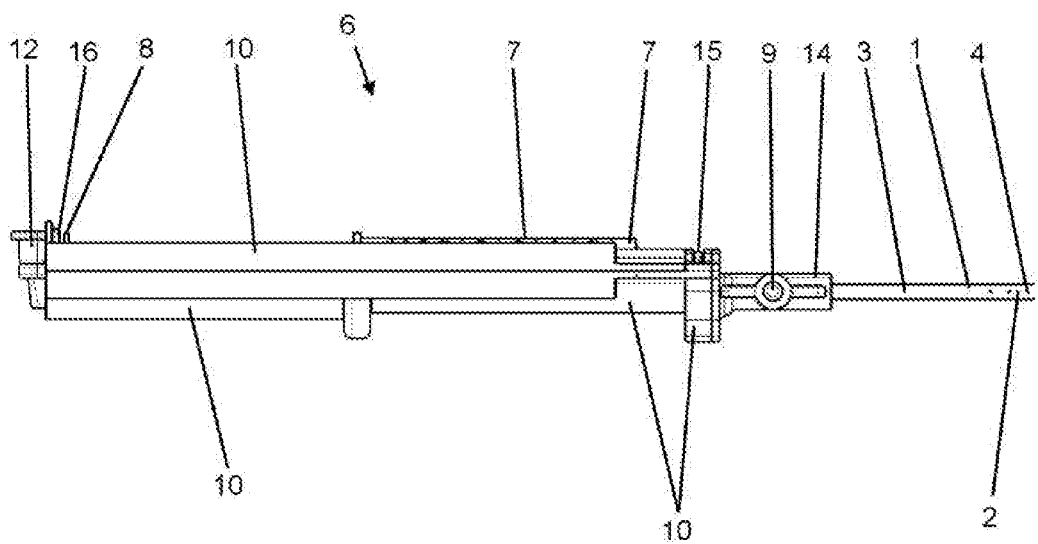
FIG. 3 is a schematic side view of a proximally arranged delivery means containing a container of the device according to FIGS. 1 and 2.
Figure 4:
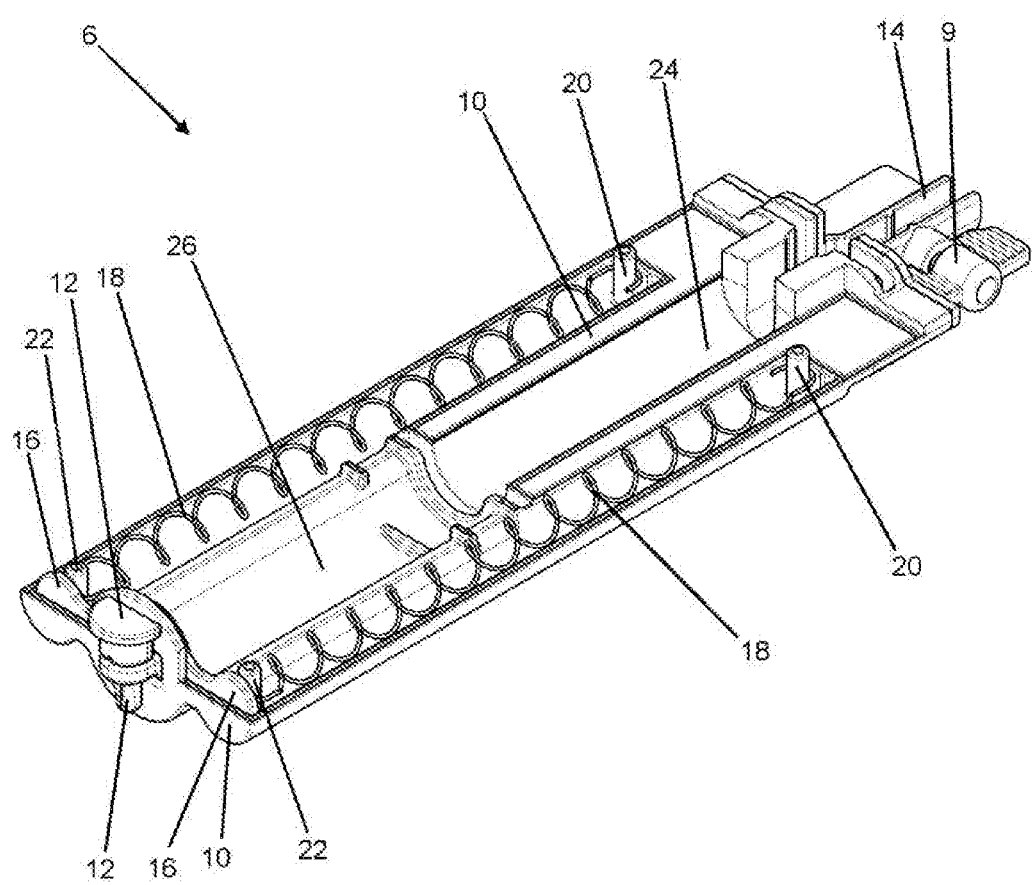
FIG. 4 is a schematic, perspective, partially sectional view of the delivery using the device according to FIGS. 1 to 3.
Figure 5:
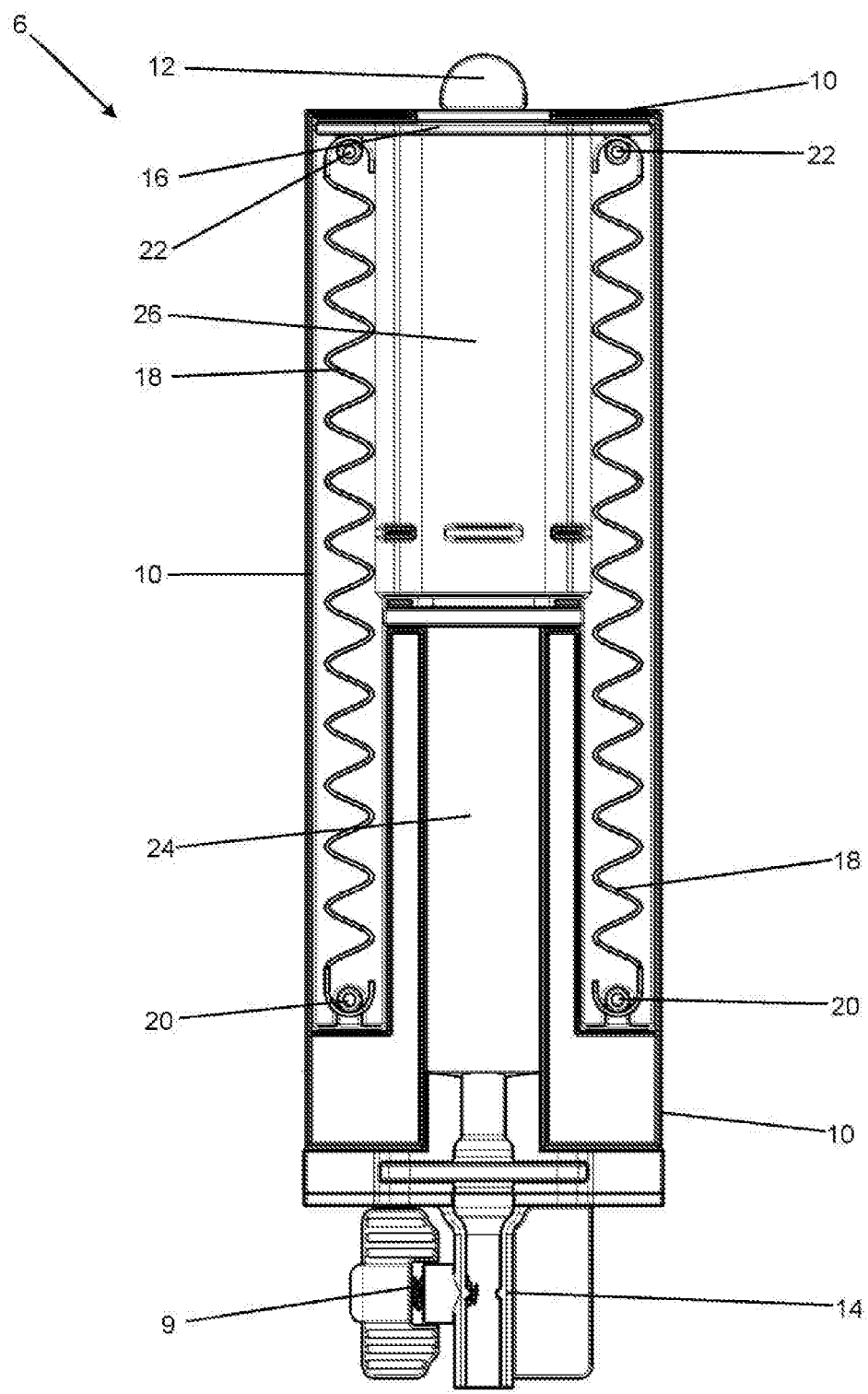
FIG. 5 is a schematic, partially sectional plan view of the delivery means according to FIG. 4 in the tensioned state.
Figure 6:
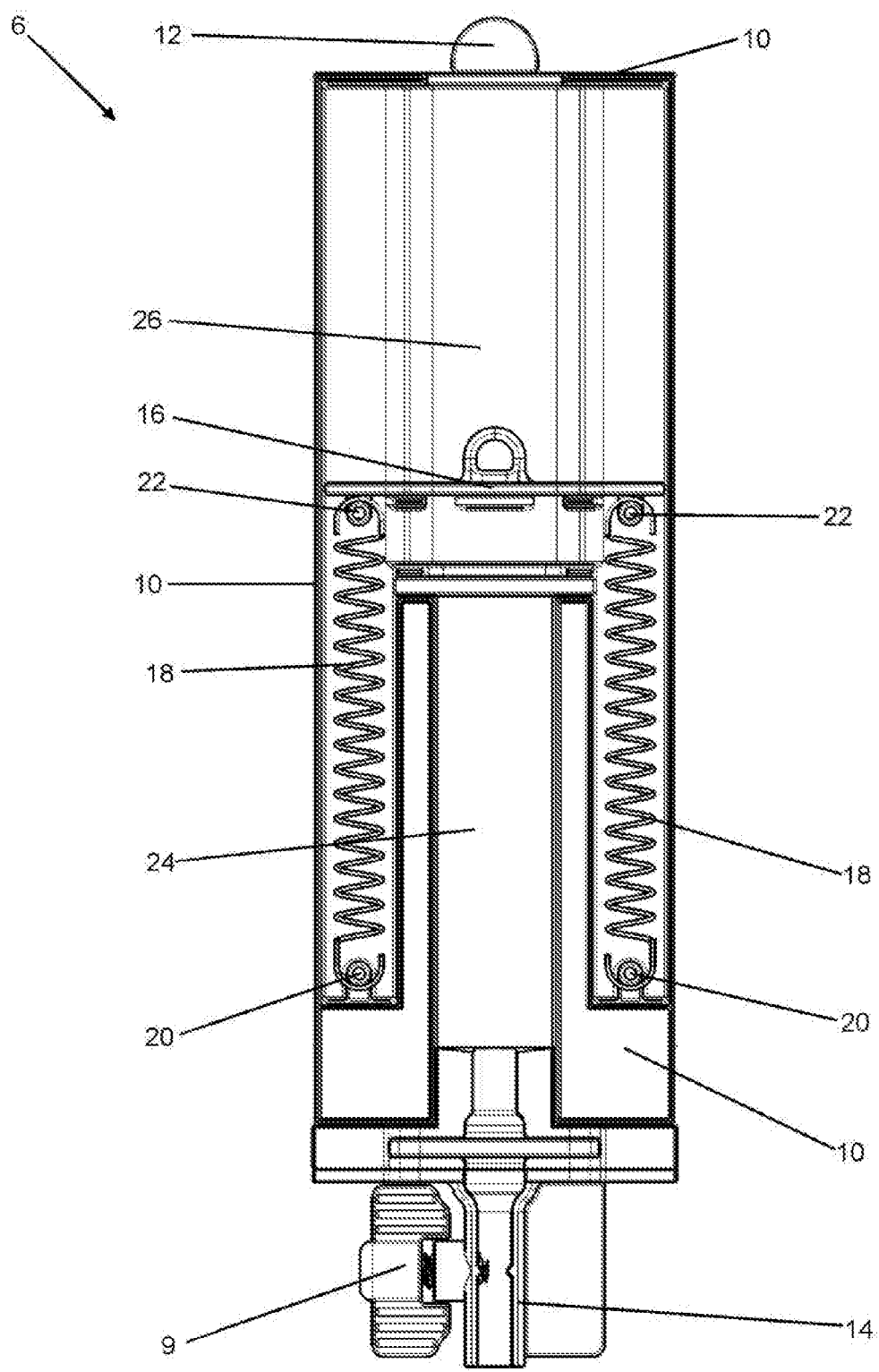
FIG. 6 is a schematic, partially sectional plan view of the delivery means according to FIG. 4 in the tensioned state.
Figure 7:
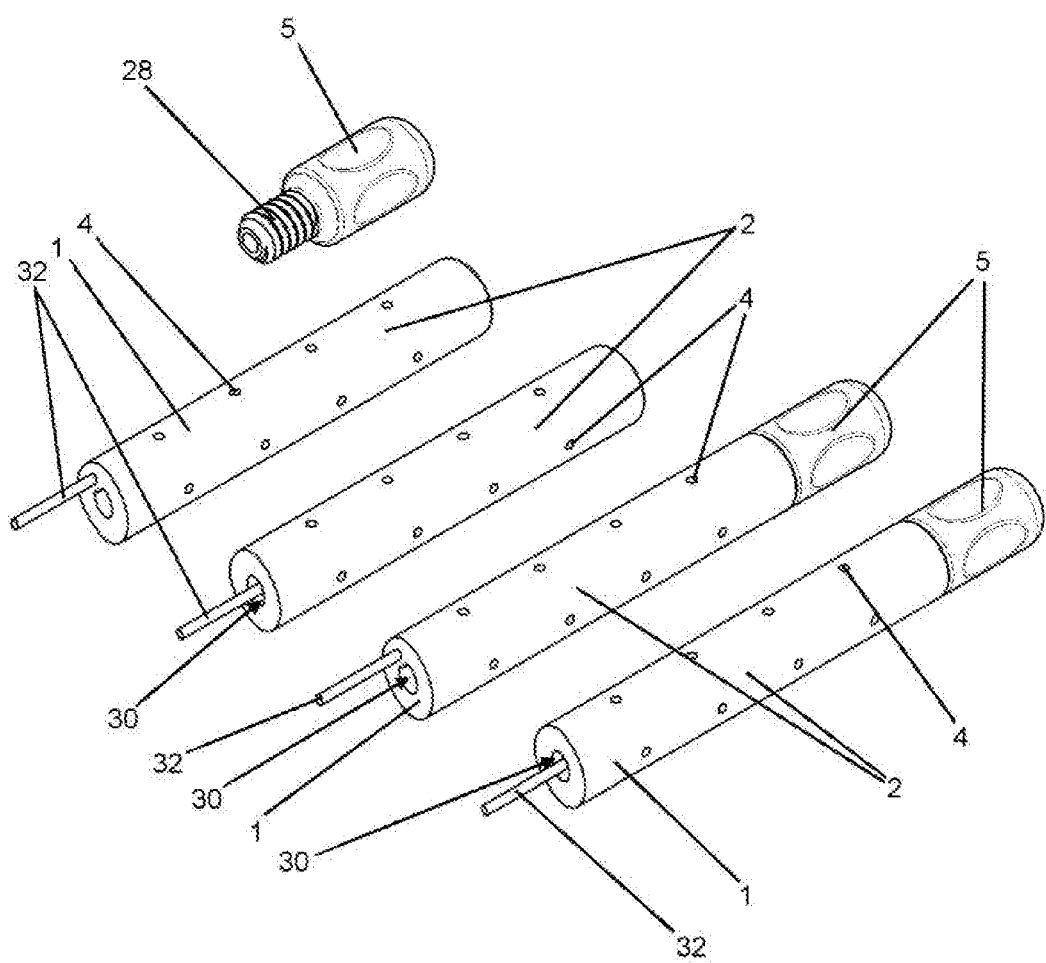
FIG. 7 illustrates a plurality of schematic, perspective views of distal hose portions of two devices according to the embodiment in the open and closed states.
Figure 8:
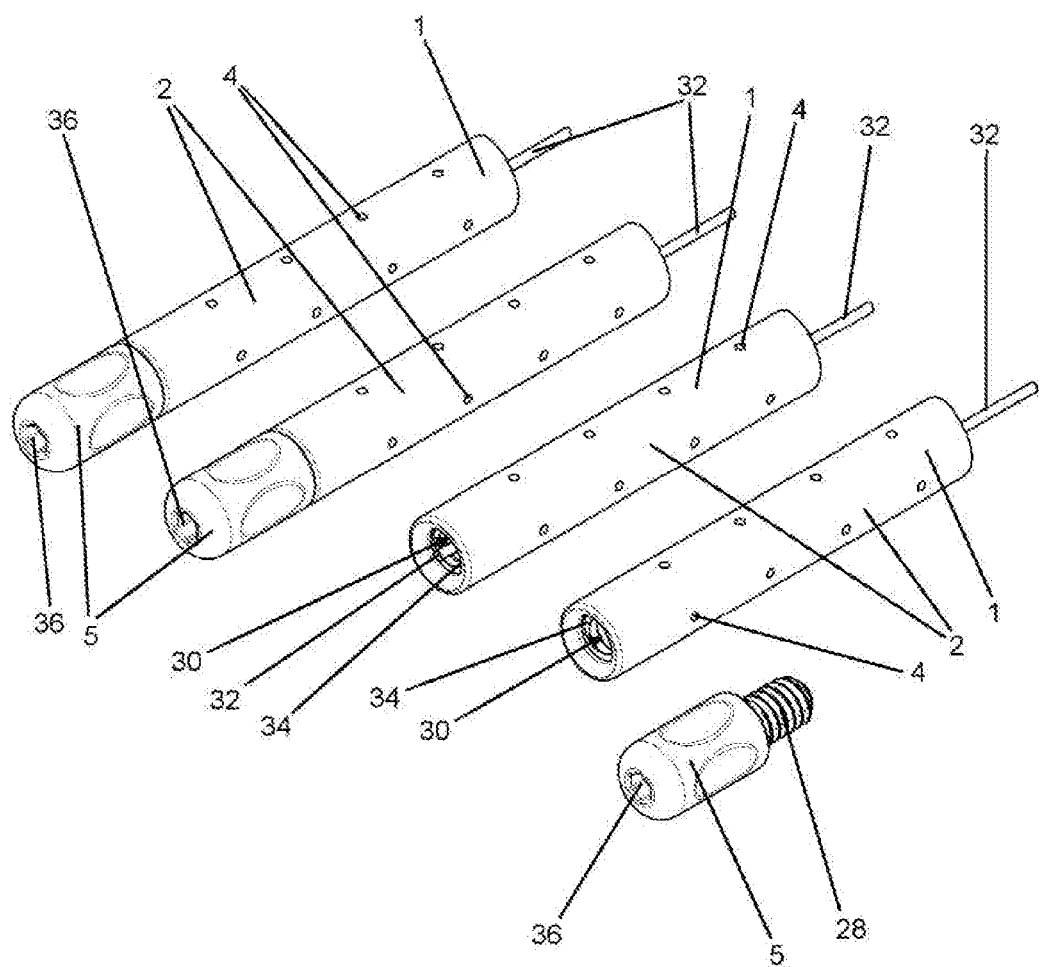
FIG. 8 illustrates a plurality of schematic, perspective views of the distal hose portions of the two devices according to FIG. 7 in the open and closed states.

The orifices 4 may be pierced through the inner wall 40 of the hose 1, such that the material of the inner wall 40 is not punched out. As in the case of rubber-elastic membranes for containers for charging syringes, the orifices 4 in the inner wall 40 may be closed thereby (see FIG. 10). If pressure is exerted in the inner conduit 30 on a fluid therein, this pressure opens the orifices 4 in the inner walls 40 of the hose 1 (see FIG. 9) and the fluid may exit from the orifices 4, as indicated in FIG. 2 by the arrows.

The orifices 4 may be radially distributed and distributed along the entire length of the distal portion 2. The orifices 4 indicated in the exemplary embodiment in four axial directions are in this respect to be understood merely as exemplary. The hose 1 may also be adapted to the size of the cavity to be irrigated, in that it is shortened at the distal portion 2 by cutting off. The newly cut distal hose end may be sealed with the closing element 5. To this end, the closing element 5 may be inserted or screwed into the inner conduit 30.

A delivery means 6 may be arranged at the proximal side of the device. A container 7 in the form of a syringe with a plunger 8 for squeezing out the contents of the syringe may be or have been inserted into the delivery means 6. The plunger 8 may be arranged in the syringe so as to be displaceable in the axial direction and sealed fluid-tightly against the internal wall of the container 7. The delivery means 6 may have a housing 10 of a plastics material which may completely or partly close the interior of the delivery means 6 with regard to the exterior. A securing pin 12 may be inserted into an orifice at the proximal end of the housing 10.

A retainer 14 for fastening the proximal end of the hose 1 may be arranged on the distal side of the delivery means 6. To this end, a retaining disk 15 which may engage in the retainer 14 may be fastened to the hose 1.

A delivery plate 16 for pressing the plunger 8 into the container 7 may be arranged in the delivery means 6. The delivery plate 16 can be secured against the housing 10 with the securing pin 12. To this end, an eyelet may project from the housing 10 of the delivery means 6 on the proximal side of the delivery plate 16 and the delivery plate 16 may be secured against the housing 10 by insertion of the securing pin 12. The delivery plate 16 may be driven by two tensioned springs 18. The two springs 18 represent an energy storage element, in which at least the energy is stored which is needed to squeeze a medical fluid out of the container 7 and through the hose 1 and through the orifices 4 of the hose 1.

The springs 18 may be fastened at their distal ends to the housing 10 with pegs 20. At their proximal ends the springs 18 may be fastened to the delivery plate 16 with pegs 22. The springs 18 may in this way be tensioned between the pegs 20 and the pegs 22.

Inside the housing, 10 a receptacle 24 for the container 7 and a stroke space 26 for the plunger 8 may be formed. The container 7 may be fixed in the delivery means 6 by the shape of the receptacle 24. The delivery plate 16 may in this way be drawn by the springs 18 from the proximal end to the distal end of the stroke space 26 (see FIGS. 5 and 6). In the delivery means 6 the plunger 8 may be pressed with the delivery plate 16 into the container 7 under the action of the springs 18, when the securing pin 12 has been removed and the valve element 9 opened. In this way, a medical fluid contained in the container 7 may be squeezed out of the container 7 and through the hose 1 and the orifices 4 of the hose 1. The orifices 4 in the inner wall of the hose 1 may be opened with the pressure acting on the medical fluid.

The hoses 1 illustrated in FIGS. 7 to 10 may be straightforwardly applied in the device illustrated in FIGS. 1 to 6 and FIGS. 7 to 10 are thus understood to be detail representations of the first exemplary embodiment. The two variants of the hoses 1 according to FIGS. 7 to 10 differ in the arrangement of a metal wire 32, which may be arranged either in an inner conduit 30 of the hose 1 or in the hose wall. The hose 1 may in both cases be closable at its distal end with a closing element 5. The closing element 5 has a protruding cylindrical extension with an external thread 28. With the external thread 28 the closing element 5 may be screwed into the open inner conduit 30 of the hose 1. The closing element 5 in one embodiment consists of metal. The external thread 28 may cut a suitable internal thread 34 in the internal wall of the hose 1. In this way, the hose 1 may be closed in liquid-tight and pressure-tight manner at its distal end. In the distal head of the closing element 5 a hexagon socket 36 may be arranged or another screw head may be provided so as to be able to screw the closing element 5 more readily into the hose 1.

Figure 9:
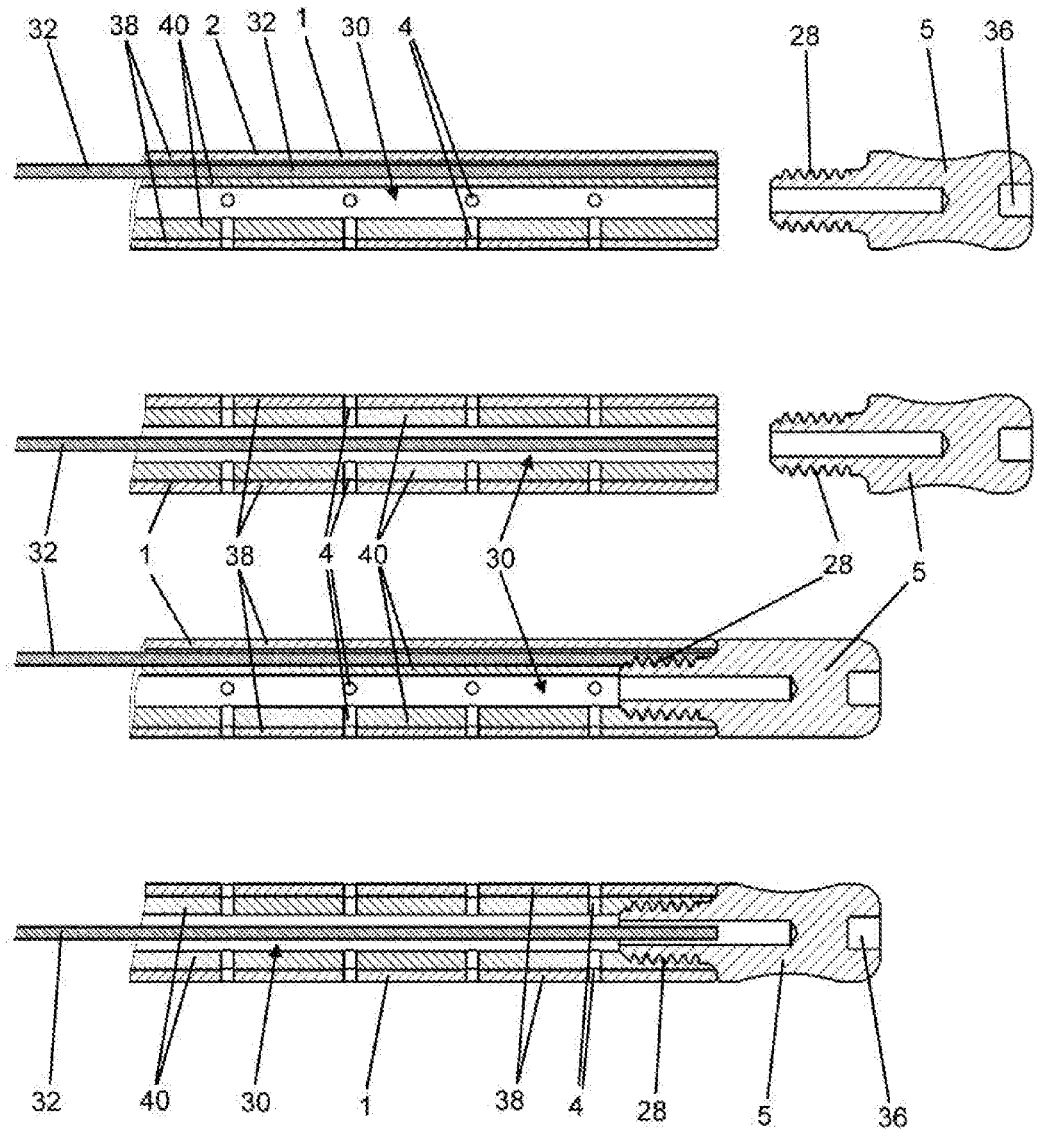
FIG. 9 illustrates four schematic cross-sectional views of the distal hose portions of the two devices according to FIGS. 7 and 8 with open orifices.
Figure 10:
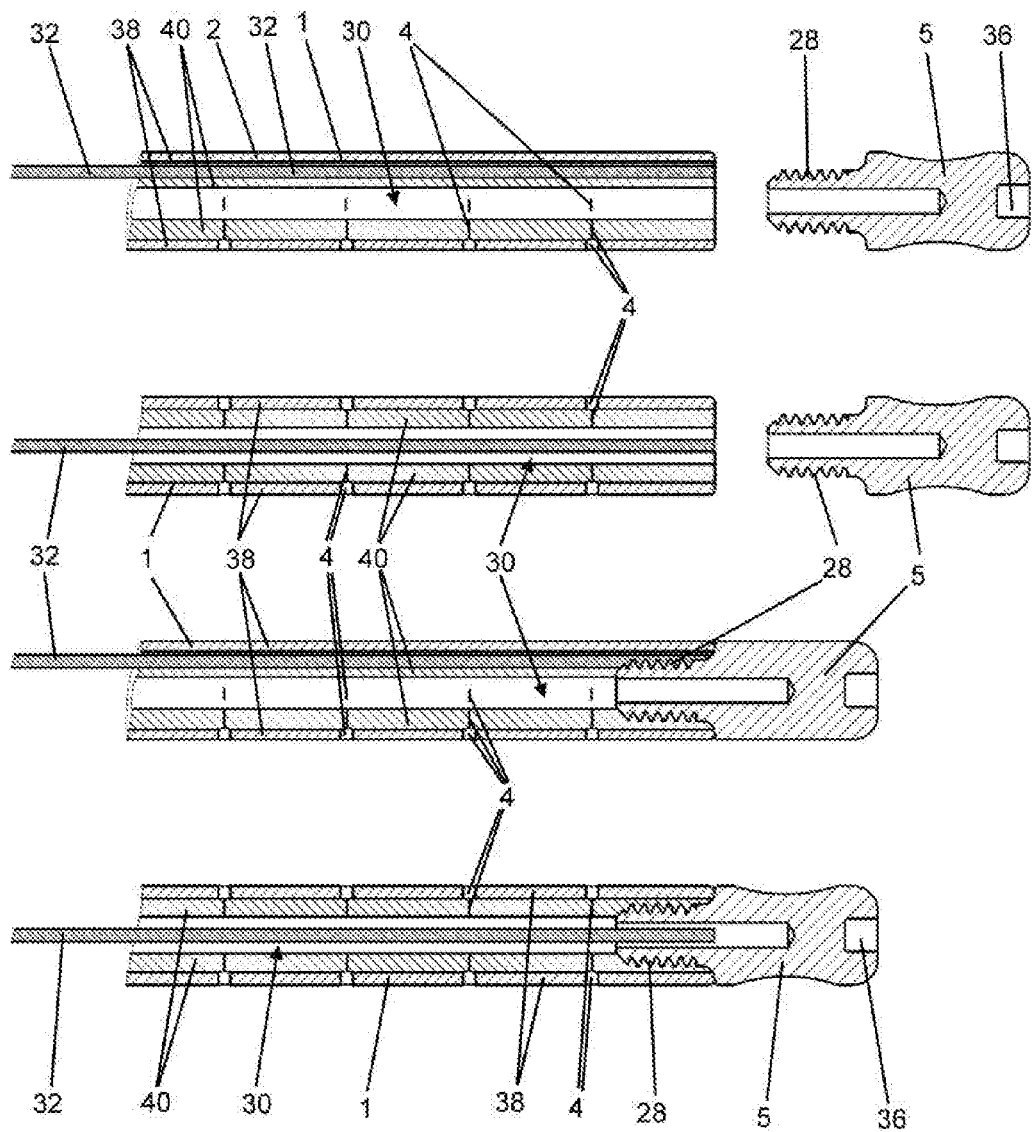
FIG. 10 illustrates four schematic cross-sectional views of the distal hose portions of the two devices according to FIGS. 7 to 9 with closed orifices.

As in the first exemplary embodiment according to FIGS. 1 to 6, the hose 1 has an outer wall 38 and an inner wall 40 (see FIGS. 9 and 10). The outer wall 38 in one embodiment completely encloses the inner wall 40. The materials for forming the outer wall 38 and the inner wall 40 may, as in the first exemplary embodiment, be selected such that the outer wall 38 is dimensionally stable and the inner wall 40 is rubber-elastic. Multiple orifices 4 extend through the outer wall 38 and the inner wall 40 as far as the inner conduit 30 of the hose 1.

If no pressure from a medical fluid acts in the inner conduit 30 of the hose 1, the material of the inner wall 40 may relax. The orifices 4 in the inner wall 40 are thereby closed in fluid-tight manner (see FIG. 10). The orifices 4 are visible in FIG. 10 as slits in the inner wall 40. Pressure on the medical fluid may result in opening of the orifices 4 in the inner wall 40. The hose 1 is not radially expanded in the process, since the outer wall 38 is able to absorb the forces. The medical fluid may exit through the opened orifices 4.

With the assistance of the metal wire 32, the hose 1 may be plastically deformed in both embodiments and retains its shape.

FIGS. 11 and 12 illustrate a further embodiment. This embodiment corresponds to the embodiments according to FIGS. 1 to 10, apart from the fact that a sealing element 42 is additionally placed on the hose 1. The reference signs and the structure of the embodiment according to FIGS. 11 and 12 thus correspond to those of the preceding embodiments. The internal structure of the hose 1, with an inner wall 40 and an outer wall 38 coaxially surrounding the inner wall 40, wherein one wall is elastically deformable by the pressure of a medical fluid while the other wall brings about radial dimensional stability is also featured in this embodiment.

The sealing element 42 may in one embodiment be axially displaceable on the hose 1 (relative to the cylindrical hose axis). According to one method, the sealing element 42 is arranged at the distal end of the proximal portion 3 of the hose 1. Then the sealing element 42 does not cover any of the orifices 4 and it is apparent to the user where the proximal portion 3 ends or where the adjacent distal portion 2 of the hose 1 begins.

The sealing element 42 may be sleeve-like in shape and have an outer sleeve shape 44 and a distal sponge sleeve 46. The sponge sleeve 46 may be impregnated with an antibiotic and/or disinfecting solution. The sealing element 42 may be pushed onto an inlet orifice in a body and thereby prevent microbes from entering the inlet orifice.

In all embodiments, the closing element 5 may be simply screwed or inserted into the distal (first) hose end of the hose 1 by the medical user once the hose 1 has been shortened. In this way, the inner conduit 30 of the hose 1 is closed.

Depending on the application, a disinfecting liquid or an aqueous solution including at least one antibiotic and/or at least one antimycotic may be used as the medical fluid to be administered. In addition, the medical fluid may also contain at least one cytostatic and/or at least one chemotherapeutic agent.

For medical use of the devices according to the embodiment, the hose 1 and in one embodiment also the closing elements 5 may be made from biocompatible materials, containing X-ray opaque materials, such that the position of the hose 1 and optionally of the closing element 5 is determinable with X-ray imaging methods.

The features of one embodiment disclosed in the preceding description, as well as in the claims, figures and exemplary embodiments, may be essential both individually and in any combination for realizing the various embodiments.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A device for local administration of a medical fluid, comprising:

a hose, which is flexibly deformable and which has a hose wall;

wherein the hose wall has an outer wall of a first material which is arranged radially to an outside, and the hose wall has an inner wall of a second material, which is different than the first material and which is arranged radially inward of the outer wall and which delimits an inner conduit of the hose, wherein the outer wall and the inner wall are fixedly connected to each other over an entire surface;

wherein, in a distal portion of the hose, the hose has multiple orifices in the hose wall;

wherein the multiple orifices connect the inner conduit of the hose with surroundings of the hose, wherein the distal portion of the hose is delimited by a distal end of the hose, wherein the multiple orifices in the hose wall extend through the inner wall and through the outer wall in an aligned manner and are slit-shaped and the multiple offices are configured to be reversibly opened and closed;

wherein, in a proximal portion of the hose, the hose does not have any orifices in the hose wall which connect the inner conduit of the hose with the surroundings of the hose in a liquid-permeable manner;

the device further comprising a closing element with which the hose is closed in liquid-tight manner at the distal end of the hose, wherein the closing element is manually insertable into the distal end of the hose as a separate component; and wherein a proximal end of the hose is connectable to a container for the medical fluid, in a liquid-permeable manner, in such a way that the medical fluid is pressable out of the container through the proximal end of the hose into the inner conduit of the hose and pressed out to the surroundings of the hose through the multiple orifices.

2. The device according to claim 1, wherein the inner conduit of the hose begins at a proximal opening in the proximal end of the hose and ends at a distal opening in the distal end of the hose, wherein the distal opening of the hose is closed by the closing element.

3. The device according to claim 1, wherein the device comprises the container for the medical fluid, wherein the container comprises a hollow cylinder with a plunger displaceable axially in the hollow cylinder, the plunger closing a first end of the hollow cylinder, wherein the hollow cylinder has a discharge opening at an opposite end from the first end, the discharge opening being connectable with the proximal end of the hose via a manually operable valve element for regulating the flow velocity of the medical fluid.

4. The device according to claim 3, wherein a medical fluid or a pharmaceutical fluid is contained in the container.

5. The device according to claim 1, wherein the device has a delivery means, with which the medical fluid is pressable out of the container into the hose if the container is connected to the hose, through the inner conduit of the hose and through the multiple orifices into the surroundings of the hose.

6. The device according to claim 5, wherein the delivery means has an energy storage element, or at least one tensioned spring, wherein the delivery means is drivable with energy from the energy storage element or from the at least one tensioned spring, wherein a plunger is drivable with the energy storage element or with the at least one tensioned spring in a hollow cylinder of the container towards an opposing discharge opening.

7. The device according to claim 1, wherein the sum of cross-sectional areas of all the multiple orifices are at most as large as a cross-sectional area of the inner conduit.

8. The device according to claim 1, wherein the multiple orifices in the outer wall of the hose wall are open irrespective of a pressure applied by the medical fluid, while the multiple orifices in the inner wall of the hose wall are closed when no pressure is applied by the medical fluid and are openable in a fluid-permeable manner by applying pressure on the medical fluid.

9. The device according to claim 1, wherein the outer wall of the hose wall is configured to absorb a pressure from the medical fluid in the inner conduit imparted via the inner wall of the hose wall, without expanding radially by more than 1%.

10. The device according to claim 1, wherein the hose is configured to expand radially by at most 1 percent under an internal pressure of 500 kPa relative to normal pressure.

11. The device according to claim 1, wherein the closing element has a conical or cylindrical projection which is inserted or screwed into the hose, such that the hose is clamped in the region of the distal end of the outer hose by the projection in such a way that the hose is closed in fluid-tight manner at the distal end of the hose, wherein the conical or cylindrical projection has ribs on the outside of the projection or the conical or cylindrical projection has an external thread, wherein the external thread or the conical or cylindrical projection has a larger external diameter then the internal diameter of the hose.

12. The device according to claim 1, wherein the multiple orifices in the hose wall each have a diameter of at most 100 µm in the outer wall.

13. The device according to claim 1, wherein the hose is formed from a coaxial form that is formed by coextrusion, wherein the inner wall consists of a rubber-elastic polymer, polyurethane or a weakly crosslinked polymer, and the outer wall consists of a non-rubber-elastic thermoplastic polymer or of a highly crosslinked polymer, or polyamide.

14. The device according to claim 1, wherein an X-ray-opaque material is present in the hose at least at the distal end of the hose and/or in the closing element, an X-ray-opaque material is present in the distal portion of the hose and/or in the closing element, is present over the entire length of the distal portion of the hose and in the closing element or is present over the entire length of the hose and in the closing element.

15. The device according to claim 1, wherein at least one metal wire, at least one metal coil and/or at least one metal mesh is/are arranged in the inner conduit of the hose and/or in the hose wall of the hose, wherein the at least one metal wire, the at least one metal coil and/or the at least one metal mesh are arranged along the entire length of the hose.

16. The device according to claim 1, wherein the closing element has the following features:
a rotationally symmetrical first body with an external thread or with circumferentially extending ribs, wherein the external thread has or the ribs have a larger external diameter than the internal diameter of the hose in areas of the hose in which the closing element is not inserted into the hose; and
a rotationally symmetrical second body with an external diameter less than or equal to the external diameter of the hose in areas of the hose in which the closing element is not inserted into the hose, wherein the axial extent of the second body is at least 5 mm;

wherein the rotationally symmetrical first body is axially connected with the rotationally symmetrical second body.

17. The device according to claim 1, wherein the closing element is screwed or pressed into the distal end of the hose and closes a cross-sectional area of the inner conduit of the hose at the distal end completely and in liquid-tight and pressure-tight manner.

18. The device according to claim 1, wherein a non-return valve element is arranged at the proximal end of the hose or in a connection to the container for the medical fluid, the valve preventing flow of the medical fluid towards the container and allows flow of the medical fluid out of the container towards the distal portion.

19. The device according to claim 1, wherein all, pairs or groups of the multiple orifices are spaced relative to one another in an axial direction of the hose.

20. The device according to claim 1, wherein the hose is plastically deformable and/or has an external diameter between 2 mm and 4 mm.

21. The device according to claim 1, wherein the first material has a greater Shore A hardness than the second material, wherein the first material has a Shore A hardness of more than 60 and the second material a Shore A hardness of less than 60.

22. The device according to claim 1, wherein each of the multiple orifices in the inner wall have a cross-sectional area that is configured to increase by a factor of two or more when a hydrostatic pressure of 500 kPa is applied to each of the multiple orifices by the medical fluid.

23. The device according to claim 1, wherein the multiple orifices in the hose wall extend through the inner wall and through the outer wall, wherein the multiple orifices in the inner wall are openable and closable in fluid-tight manner as a function of a physical quantity acting on the second material, or as a function of a pressure from the medical fluid acting on the second material, or the multiple orifices in the outer wall are openable and closable in fluid-tight manner as a function of a physical quantity acting on the first material, or as a function of a pressure from the medical fluid acting on the first material.

24. The device according to claim 1, wherein the multiple orifices in the hose wall extend through the inner wall and the second material and through the outer wall and the first material, wherein the multiple orifices are openable by elastic deformation of the second material and closable by undeforming the second material, while the multiple orifices in the first material remain open, wherein the first material is stable against deforming such that the outer wall absorbs at least some of the forces caused by the elastic deformation of the second material and thereby counteracts radial deformation of the hose.

* * * * *